(12) United States Patent
Wolter et al.

(10) Patent No.: US 9,233,992 B2
(45) Date of Patent: Jan. 12, 2016

(54) SILICIC ACID POLYCONDENSATES HAVING CYCLIC OLEFIN-CONTAINING STRUCTURES, METHOD FOR THE PRODUCTION THEREOF, AND USE THEREOF

(71) Applicant: Fraunhofer-Gesellschaft zur Foerderung der angewandten Forschung e.V., Munich (DE)

(72) Inventors: Herbert Wolter, Tauberbischofsheim (DE); Somclith Nique, Eisingen (DE); Denise Bausen, Vilters-Wangs (CH)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

(21) Appl. No.: 14/350,692

(22) PCT Filed: Oct. 9, 2012

(86) PCT No.: PCT/EP2012/069940
§ 371 (c)(1),
(2) Date: Apr. 9, 2014

(87) PCT Pub. No.: WO2013/053693
PCT Pub. Date: Apr. 18, 2013

(65) Prior Publication Data
US 2014/0249325 A1    Sep. 4, 2014

(30) Foreign Application Priority Data
Oct. 12, 2011   (DE) .................. 10 2011 054 440

(51) Int. Cl.
C07F 7/04      (2006.01)
C07F 7/18      (2006.01)
C08G 77/388    (2006.01)
C08G 77/392    (2006.01)

(52) U.S. Cl.
CPC .............. *C07F 7/1868* (2013.01); *C07F 7/184* (2013.01); *C08G 77/388* (2013.01); *C08G 77/392* (2013.01)

(58) Field of Classification Search
CPC ............................. C07F 7/184; C08G 77/388
USPC ..................................................... 556/420
See application file for complete search history.

(56) References Cited

U.S. PATENT DOCUMENTS

| 5,532,398 | A | 7/1996 | Wolter et al. |
| 5,717,125 | A | 2/1998 | Wolter et al. |
| 6,106,606 | A | 8/2000 | Gellermann et al. |
| 6,222,055 | B1 | 4/2001 | Wolter et al. |
| 6,447,907 | B1 | 9/2002 | Wolter et al. |
| 6,794,527 | B1 | 9/2004 | Wolter et al. |
| 2004/0023040 | A1 | 2/2004 | Gellermann et al. |
| 2008/0187499 | A1 | 8/2008 | Wolter et al. |
| 2008/0317794 | A1 | 12/2008 | Gellermann et al. |
| 2008/0319127 | A1* | 12/2008 | Wolter ............... 524/588 |
| 2009/0023883 | A1 | 1/2009 | Wolter |
| 2011/0063567 | A1* | 3/2011 | Domschke ........ C08F 290/067 351/159.34 |
| 2011/0082250 | A1 | 4/2011 | Wolter |
| 2014/0100349 | A1 | 4/2014 | Wolter et al. |

FOREIGN PATENT DOCUMENTS

| DE | 4011044 C2 | 10/1991 |
| DE | 4416857 C1 | 6/1995 |
| DE | 19627198 C2 | 1/1997 |
| DE | 19643781 C2 | 4/1998 |
| DE | 19832965 A1 | 2/2000 |
| DE | 19910895 A1 | 9/2000 |
| DE | 10018405 B4 | 10/2001 |
| DE | 10041038 B4 | 3/2002 |
| DE | 10132654 A1 | 10/2002 |
| DE | 10349766 A1 | 6/2005 |
| DE | 102005018351 B4 | 11/2006 |
| DE | 102005061965 A1 | 7/2007 |
| DE | 102011050672 A1 | 11/2012 |
| WO | WO2005040249 A1 | 5/2005 |

* cited by examiner

*Primary Examiner* — Porfirio Nazario Gonzalez
*Assistant Examiner* — Kofi Adzamli
(74) *Attorney, Agent, or Firm* — Duane Morris LLP

(57) ABSTRACT

The present invention relates to silicic acid (hetero)polycondensates comprising structural units of a following formula (1)

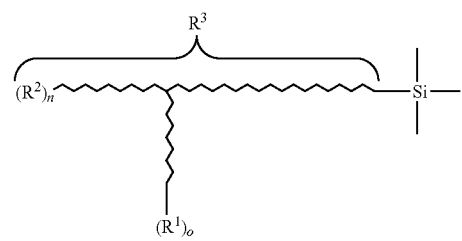

wherein radicals, indices, and bonding symbols have the following meaning:
$R_1$ refers to a group that is accessible to a thiol-ene polyaddition when a thiol is added and can also be polymerized by a ROMP (ring opening metathesis polymerization),
$R_2$ is selected from (a) organically polymerizable groups that are available to a thiol-ene polyaddition when a thiol is added, but not to a ROMP, (b) —$COOR^8$ with $R^8$ equal to $R^4$ or $M_{1/x}^{x+}$, (c) —OH or COOH, and (d) —$(O)_b P(O)(R^5)_2$, wherein b is equal to 0 or 1, —$SO_3 M_{1/x}^{x+}$, $NR^7_2$ or $NR^{7+}_3$.

21 Claims, No Drawings

SILICIC ACID POLYCONDENSATES HAVING CYCLIC OLEFIN-CONTAINING STRUCTURES, METHOD FOR THE PRODUCTION THEREOF, AND USE THEREOF

The present invention relates to silicic acid (hetero)polycondensates with cyclical olefinic structures, from which polymeric materials with broadly adjustable moduli of elasticity can be produced with a high level of elastic strain (i.e. not brittle) and therefore a high resistance to fracture. The invention also relates to the production of condensates as well as their possible uses.

These types of materials are necessary, e.g. in oral medicine, which poses very different requirements with respect to the modulus of elasticity with a given material base through minimal modifications within the basic structure, whereas the hardening mechanisms should respectively be the same to the extent possible. One goal in this regard is to reduce the overall number of necessary material classes or types so as to maintain the potential for allergies, e.g. in oral surgery and dentistry, as minimal as possible. Simple principles of synthesis without complicated, sensitive reactions and, thus, a material base that is likewise easily accessible on a large-scale are particularly important in this regard. As such, minimal shrinkage, a high sensitivity to the selected hardening parameters as a possibility for a sensitive adjustment of the hardening speed while still providing a good shelf life, the absence of potentially toxic or allergenic monomers in the polymeric products, as well as potentially a simple, uncomplicated ability to be sterilized are also preferable.

In the area of dental materials, though not exclusively there, it is essential to be able to provide a range of materials that can be used for the same purposes and have the same physical and mechanical properties, wherein, however, these properties must be adapted to specific, and frequently even individual requirements to the smallest detail. Examples are the matrix hydrophily, contraction, and reactivity to substrates or further matrix or composite elements, such as dental tissue, co-reactants or reactants in ionomer composites. In this case, minimal changes frequently have a great effect. If the specialist, for example a dentist or an orthodontist, working with these materials can resort to a structured range of materials necessary for his own purposes, he will be able to select the appropriate material for each individual application.

In the last 20 years, a variety of silanes have been developed, which are not only hydrolytically condensable, but can also be subjected to an organic polymerization, for example, via reactive double bonds or cyclical olefinic structures. Through the number of double bonds or rings as well as the presence of potentially additional reactive groups, a multitude of condensates, polymers, and composites can be produced from or with these silanes, which are suitable for a variety of applications. Examples of such materials are revealed in DE 44 16 857 C1, DE 196 27 198, and DE 103 49 766 A1. However, these materials do not meet the previous demands.

The purpose of the invention is to create a remedy and to provide silicic acid (hetero)polycondensates (also referred to as siloxanes or "Ormocer®e"), which, assuming a basic material, offer benefits through reactive groups introduced at a controlled position with respect to their variability upon further processing (hardening), e.g. through staged hardening speeds, and/or based on various etching or bonding properties or various moduli of elasticity. Moreover, in preferred embodiments, reactive groups should be available in the same material in order to be able to apply various hardening mechanisms. These materials should be suitable for multiple purposes, including in dentistry and in the medical industry, e.g. as dental restoration, prophylaxis or bone replacement material.

In solving the given problem, the present invention provides a silicic acid (hetero)polycondensate comprising structures of a following formula (1)

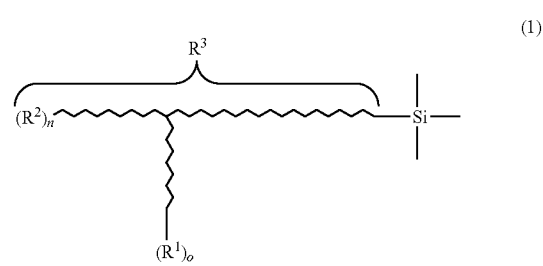

wherein the radicals and indices have the following meaning:

$R^1$ refers to a group that is available to a thiol-ene polyaddition when a thiol is added and can also be polymerized by a ROMP (ring opening metathesis polymerization), $R^2$ is selected from (a) available to a thiol-ene polyaddition when a thiol is added, but not to a ROMP, (b) —COOR$^8$ with R$^8$ equal to $R^4$ or $M_{1/x}^{x+}$, (c) —OH, —COOH (d) —(O)$_b$P(O)(R$^5$)$_2$, wherein b is equal to 0 or 1, —SO$_3$M$_{1/x}^{x+}$, NR$^7_2$ or NR$^{7+}_3$, whereas $M^{x+}$ is an x-fold positively charged metal cation with x preferably equal to 1, 2, 3 or 4, $R^4$ is a non-substituted or substituted hydrocarbon radical, the radicals $R^5$ represent a non-substituted or substituted hydrocarbon radical or OR$^6$ and $R^6$ is hydrogen or a non-substituted or substituted hydrocarbon radical, $R^7$ has either the same meaning as $R^4$ or two radicals $R^7$ together represent a double-bonded, potentially randomly substituted, potentially unsaturated (even aromatic) hydrocarbon group;

accordingly NR$^7_2$ and NR$^{7+}_3$ can, e.g. be a pyridine radical or the radical of a cyclical ammonium compound or a pyridinium derivative or the like. Radicals $R^2$ with the meaning of NR$^7_2$ or NR$^{7+}_3$ can have essential additional functions in a resin produced pursuant to the invention. Thus, in the case of NR$^7_2$, an activator molecule arises, which can be used for a redox-hardening. Compounds or resins with NR$^{7+}_3$ radicals demonstrate an antimicrobial effect.

$R^3$ represents a radical bonded to a silicon atom of said formula (1) by a carbon atom, to which the radical $R^1$ is bonded o-fold and the radical $R^2$ is bonded n-fold and which is equivalent or has different meanings in the same condensate, each of the indices, n and o represents 0, 1, 2 or greater than 2 with the stipulation that n+o represents at least 2, wherein each radical $R^3$ of said structure (1) must have at least one group $R^1$ or one group $R^2$ with the meaning specified in (a) and (i) then, if the radicals $R^3$ are equal, (x) each radical has at least one group $R^1$ and either one group $R^2$ with the meaning specified in (a) or a second group $R^1$ (i.e. in these cases, o=2 or greater than 2), wherein, in both cases, n must be at least 1 or
(xx) if, in addition, n is equal to 0, at least two groups $R^1$ have a different meaning, and
(ii) then, if the radicals $R^3$ are different, a first part of the radicals has at least one group $R^1$ and one of the following two conditions must be complied with:
(x) an additional part of the radicals has at least one group $R^2$ with the meaning specified in (a) or (d), and
(xx) two different radicals $R^3$ have at least one group $R^1$ (i.e. o=1 or greater than 1).

In the event that n represents a number >1, the groups $R^2$ can have different meanings.

In said formula (1), the zigzag line represents a backbone of a hydrocarbon radical bonded to the silicon atom by a carbon atom, wherein this backbone can be interrupted at will by heteroatoms or linkage groups or other groups containing heteroatoms. Examples are interruptions by —S—, —O—, —NH—, —C(O)O—, —NHCH(O)—, —C(O)NH— and the like. Due to the fact that the structure of the backbone of this radical is not essential for the purpose of the invention, the specialist may make a random selection in this case.

Said group $R^1$ is preferably a cycloolefinic, more preferably a bi-cycloolefinic radical, and particularly preferably a norbornenyl radical. Suitable examples are:

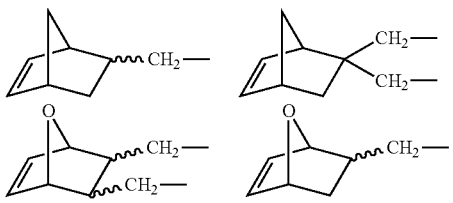

In this regard, the cycloolefinic radical can be bonded directly to a carbon network of the hydrocarbon radical or via a linkage group. Examples regarding which groups or radicals of this radical can be bonded to the silicon can be found in DE 196 27 198 A1 where the following are mentioned: —(CHR$^6$—CHR$^6$)$_n$— with n=0 or 1, —CHR$^6$—CHR$^6$—S—R$^5$—, —C(O)—S—R$^5$—, —CHR$^6$—CHR$^6$—NR$^6$—R$^5$, —Y—C(S)—NH—R$^5$, —S—R$^5$—, —Y—C(O)—NH—R$^5$—, —C(O)—O—R$^5$—, —Y—CO—C$_2$H$_3$(COOH)—R$^5$—, —Y—CO—C$_2$H$_3$(OH)—R$^5$— and —C(O)—NR$^6$—R$^5$—, whereas R$^5$ can be an alkylene, arylene, arylenalkylene or arylalkylene, and R$^6$ can be hydrogen, alkyl or aryl with preferably 1 to 10 carbon atoms.

If the groups $R^2$ represent an organically polymerizable group, this means that this group is accessible to a polyreaction, for which reactive double bonds transform into polymers (addition polymerization or chain-growth polymerization) under the influence of heat, light, ionizing radiation or redox-induced (e.g. with an initiator (peroxide or the like) and an activator (amine or the like)). During this polymerization, neither a separation of molecular components occurs nor a migration or rearrangement. Moreover, these groups should particularly preferably be accessible to a thiol-ene polyaddition when a thiol is added. The reactive double bond(s) of this group can be randomly selected, for example, a vinyl group or component of an allyl or styryl group. Preferably, it/they are a component of a double bond, which is accessible to a Michael addition, thus containing an activated methylene group as a result of the proximity to a carbonyl group. In turn, preferred among these are acrylic acid and methacrylic acid groups or derivatives. The group $R^2$ normally contains at least two and preferably up to approx. 50 carbon atoms. The organically polymerizable groups $R^2$ can be bonded directly to the carbon network of the hydrocarbon radical or via a random linkage group.

The term "(meth)acrylic . . . " presently means that in each case it can be dealing with the respective acrylic or the respective methacrylic compound or a mixture of both. The present (meth)acrylic acid derivatives comprise the acids themselves, potentially in an activated form—esters, amides, thioesters, and the like.

In all cases, the hydrocarbon radicals of the present invention may be, for example, straight-chain, branched or cyclical alkylene, alkenylene, aryl, alkylaryl or arylalkyl radicals. The non-cyclical radicals frequently have 1 to 100, preferably 1 to 30, and more preferably 1 to 4 or 6 carbon atoms, while with the other radicals this is 5 to 100, preferably 6 to 50, and more preferably 6 to 12 carbon atoms.

At least one of the three bonds of the Si atom not further identified represents an oxygen bridge to other silicon atoms or other metal atoms if dealing with a heterocondensate. The other two bonds may also have this meaning; alternatively, they can represent an OH group, a hydrolysable group or a radical bonded to the silicon atom via carbon, which may have random properties. This may vary from those of the radical $R^3$ and, e.g. be a substituted or non-substituted hydrocarbon radical; alternatively, one or even two such radicals may have the meaning of $R^3$.

The indices n and o can independently represent 0, 1 or 2, though potentially even 3, 4 or more. The only condition is that n and o together are 2 or greater than 2. Frequently, o is equal to 1.

In two independent, specific embodiments, n equals 2 or greater than 2 and each $R^2$ means the same as COOH or OH.

In another embodiment that is likewise independent from other embodiments, the silicic acid (hetero)polycondensate contains at least two different groups $R^1$. They can be substituents for one and the same radical $R^3$ in a preferred variation; in another preferred variation, the polycondensate contains different radicals $R^3$ that respectively carry different groups $R^1$. Of the mentioned embodiments, it is necessary in turn to particularly highlight those, in which there is also at least one group $R^2$. This can be particularly preferably selected from COOH or OH.

The conditions for the distribution of groups $R^1$ and $R^2$ in the radical or radicals $R^3$ are selected such that—in the silicic acid (hetero)polycondensate pursuant to the invention—either
(i) at least two different reactive organically polymerizable groups are present, which are accessible to a thiol-ene reaction, and/or
(ii) different radicals $R^3$ are present, which respectively have one group $R^1$ as well as a second group $R^2$, whereas at least radicals $R^2$ differ from each other in various radicals $R^3$, and/or
(iii) each radical $R^3$ has at least two groups $R^1$ in addition to another group $R^2$, which may be different in various radicals $R^3$, and/or
(iv) at least two different groups $R^1$ accessible to a ROMP are present.

Due to this composition, the silicic acid (hetero)polycondensates pursuant to the invention have the following advantages:

If two different reactive organically polymerizable ($R^2$) and/or ($R^1$) groups accessible to a ROMP are present, groups are available that can be hardened in a staged manner, potentially through various hardening mechanisms, and thus with a different speed as well.

A mixed system, i.e. a condensate with different groups $R^3$, can be specifically and easily adjusted to each other through the ratio of output materials. Thus, a number of similar condensates, which differ with respect to their physical properties, can be produced based on a single output material. Condensates with at least two groups on a radical $R^3$, which are respectively accessible to a thiol-ene addition, can be hardened to an organic polymer with a very dense organic cross-link. Other hardening reactions can be finely graduated as well, such as ROMP or polymerization through the polyaddition of radicals representing (a) (and particularly (meth)acrylic groups form double bonds). In cases, in which groups $R^2$ have the meanings in (b) to (d) and n is not equal to 0, the condensates pursuant to the invention demonstrate an improvement of adhesion, etching effect, matrix hydrophily of mechanical or antibacterial properties, and/or there are benefits when hardening. If necessary, free hydroxy groups or carboxyl groups can ultimately be used for coupling (adding) additional functional groups, e.g. through esterification or reaction with isocyanate. If di-, tri- or higher functional (e.g. tetra-functional) reactants, such as di or triisocyanate or di or tricarboxylic acids are used, the condensate can be organically cross-linked through yet another mechanism.

In some condensates, group $R^2$ can be present consistent with one group per radical $R^3$ (n is then equal to 1 in formula (1)); however, the invention provides tailored condensates as well, in which one such group is present only in a part of radicals $R^3$ or in which multiple, different such groups are present on different radicals $R^3$. This even further increases the variability of condensates with respect to the specified parameters. In many embodiments, the benefits, which arise due to the presence of organically polymerizable groups, and those that arise due to the presence of groups with a meaning pursuant to (b) to (d), exist as a combination.

The branching of the hydrocarbon backbone depicted in formula (1)—shown with the diverging zigzag line—is optional. In specific embodiments, radical $R^1$ can namely be a substituent, which is directly bonded to an atom of the backbone of $R^3$. One example is the case, wherein $R^1$ is a norbornenyl radical, which is bonded directly to a carbon atom from the backbone of the Si—C bonded radical.

The silicic acid polycondensate may either have only silicon atoms in an inorganic silicic acid structure or may also contain other metal atoms in addition to silicon atoms, as known from the state of the art, e.g. boron, aluminum, titanium, zirconium, or tin, which are added to the condensate through respective alkoxides or the like. The latter involves silicic acid hetero-polycondensates. The term "silicic acid (hetero)polycondensates" includes both variations.

To achieve the silicic acid (hetero)polysiloxanes pursuant to the invention, we may assume, for example Silicic acid (hetero)polycondensates that were produced from silanes of a general formula (A) through hydrolysis:

$$\{X_aR_bSi[R'(A)_c]_{(4-a-b)}\}_xB \qquad (A)$$

wherein said radicals have the following meaning:
X: hydrogen, halogen, hydroxy, alkoxy, acyloxy, alkylcarbonyl, alkoxycarbonyl or —NR''$_2$;
R: alkyl, alkenyl, aryl, alkylaryl or arylalkyl;
R': alkylene, arylene or alkylenarylene;
R'': hydrogen, alkyl or aryl;
A: O, S, PR'', POR'' or NHC(O)O;
B: straight-chain or branched out organic radical that is derived from a compound with at least three C=C double bonds and 5 to 50 carbon atoms;
a: 1, 2 or 3;
b: 0, 1 or 2;
c: 0 or 1;

x: whole number, the maximum value of which corresponds to the number of double bonds in the compound B minus 1.

Such silanes and polycondensates are revealed in DE 40 11 044 A1.

Silicic acid (hetero)polycondensates that were produced from silanes of a general formula (B) through hydrolysis and condensation:

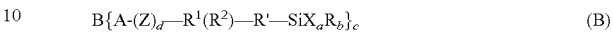

wherein said radicals and indices have the following meaning:
A=O, S, NH or C(O)O;
B=straight-chain or branched out organic radical that is derived from a compound with at least one C=C double bond and 4 to 50 carbon atoms;
R=alkyl, alkenyl, aryl, alkylaryl or arylalkyl;
R'=alkylene, arylene, arylenalkylene or alkylenarylene with respectively 0 to 10 carbon atoms, wherein these radicals can be interrupted by oxygen and sulfur atoms or by amino groups;
R$^1$=nitrogen, alkylene, arylene or alkylenarylene with respectively 1 to 10 carbon atoms, wherein these radicals can be interrupted by oxygen or sulfur atoms or by amino groups;
R$^2$=OH or COOH;
X=hydrogen, halogen, hydroxy, alkoxy, acyloxy, alkylcarbonyl, alkoxycarbonyl or —NR''$_2$;
R''=hydrogen, alkyl or aryl;
Z=CO or CHR, with R equal to H, alkyl, aryl or alkylaryl;
a=1, 2 or 3;
b=0, 1 or 2.

Such silanes and silicic acid polycondensates are revealed in DE 44 16 857 C1.

Silicic acid (hetero)polycondensates that were produced from silanes of a general formula (C) through hydrolysis and condensation:

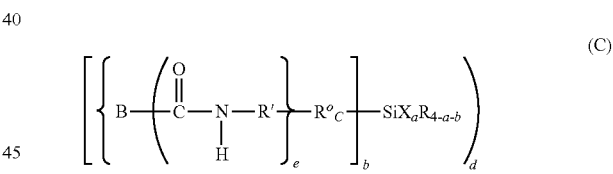

wherein said radicals and indices have the following meaning:
B=organic radical with at least one C=C double bond;
R=alkyl, alkenyl, aryl, alkylaryl or arylalkyl;
R° and R' respectively=alkylene, alkenylene, arylene, alkylenarylene or arylenalkylene;
X=hydrogen, halogen, hydroxy, alkoxy, acyloxy, alkylcarbonyl, alkoxycarbonyl or —NR''$_2$ with R'' equal to hydrogen, alkyl or aryl;
a=1, 2 or 3
b=1, 2 or 3, with a+b=2, 3 or 4;
c=0 or 1;
d=1, 2, 3, 4, 5, 6, 7, 8, 9 or 10;
e=1, 2, 3 or 4 with e=1 for c=0,
with the condition that either e or b must be >1 or B is an organic radical with more than one C=C double bond.

Said silanes of formula (C) and the silicic acid polycondensates capable of being derived thereof are revealed in DE 199 10 895 A1.

Silicic acid (hetero)polycondensates that were produced from silanes of a general formula (D) through hydrolysis and condensation:

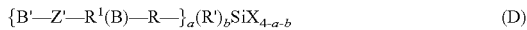

(D)

wherein said radicals and indices have the following meaning:

R is an alkylene, arylene or alkylenarylene group, which can be interrupted by one or more oxygen or sulfur atoms or carboxyl or amino groups, or can carry such atoms/groups on its end facing away from the silicon atom;

$R^1$ is an alkylene, arylene or alkylenarylene group substituted by Z', which can be interrupted by one or more oxygen or sulfur atoms or carboxyl or amino groups, or can carry such atoms/groups on one of its ends;

R' is an alkyl, alkenyl, aryl, alkylaryl or arylalkyl group;

B and B' can be equal or different; both radicals have the meaning of a straight-chain or branched organic group with at least one C=C double bond and at least two carbon atoms;

X is a group, which can enter a hydrolytic condensation reaction through the formation of Si—O—Si bridges;

Z' have the meaning —NH—C(O)O—, —NH—C(O)— or —CO(O)—, wherein both of the initially mentioned radicals are bonded to radical B' by an NH group, while a carboxylate group can point in both directions;

a represents 1 or 2 and b is 0 or 1.

Such silanes and polycondensates are revealed in DE 103 49 766 A1; they can be subsumed under structure (1), wherein $R^2$ is an organically polymerizable radical.

Silicic acid (hetero)polycondensates that were produced from silanes of a general formula (E) through hydrolysis and condensation:

(E)

wherein said groups, radicals, and indices have the following meaning:

B is at least a double-bonded, straight-chain or branched group with at least one organically polymerizable radical and at least 3 carbon atoms, X is a radical or OH capable of being hydrolyzed off a silicon atom, R and R' are independently alkyl, alkenyl, aryl, alkylaryl or arylalkyl and potentially substituted, Y is Cl, OH or OR', a is 0, 1, 2 or 3, b is 0, 1 or 2, a+b together are 1, 2 or 3, c is 0, 1 or 2, d is 0, 1 or 2, c+d together are 2, m is at least 1, with the stipulation that m is not greater than 1 if a+b represents 1 or 2, n is at least 1, o is 0 or 1, and p is 0 or 1.

Silanes of formula (E) and silicic acid polycondensates derived thereof are revealed in DE 101 32 654 A1. They fall under structure (1), wherein $R^2$ is a phosphorous radical, for example a phosphorous acid.

We can also assume reaction products of these silicic acid polycondensates, namely particularly those that were produced through one or more reactions with compounds, which connect to groups containing double bonds B or B' of the radicals in condensates (A) to (E). In the process, silicic acid polycondensates may form that have at least two radicals $R^2$, as defined above, whereas one of these radicals contains or is an organically polymerizable group having a C=C double bond, whereas, however, at least one of these radicals is located further away from the silicon atom than in the output silicic acid polycondensate. In this context, the number and meaning of radicals $R^2$ as well as their distance to the silicon atom can be different in various radicals bonded to the silicon atom via carbon. This is described in patent application DE 10 2011 050 672.1. The silicic acid polycondensate used as an output material can be produced from the respective silanes through hydrolytic condensation.

Sometimes silicic acid polycondensates do not serve as the output material, but rather respective silanes. In these cases, hydrolytic condensation occurs at the proper spot in the reaction sequence.

The reaction of the respective to the silicic acid polycondensates pursuant to the invention occurs in each case to the fact that a reagent (Y), which is selected from cyclopentadiene, furan, cyclohexadiene, as well as materials, from which in situ one of these three compounds can arise, connects to groups B and/or B' of the aforementioned condensates (A) to (E) or to comparable condensates with radicals B and/or B', as defined for (A) to (E), or to silanes that are transferrable to these condensates, i.e. to groups having polymerizable double bonds. In preferred embodiments, cyclopentadiene is used as a reagent (Y). This is normally produced in situ through separation of dicyclopentadiene.

In the event that all radicals $R^3$ should be identical in the silicic acid (hetero)polycondensate pursuant to the invention, e.g. one of the previously shown condensates (or a comparable other condensate) is used as the output material for this. There are principally four various routes if the condensate pursuant to the invention should have different radicals $R^3$. In the first route, different silanes are co-condensed with suitable radicals, whereupon the co-condensate is additionally randomly converted. In the second route, a silicic acid (hetero)polycondensate, for which a preliminary stage of the output material is involved, or its underlying silane is subjected to a non-random reaction such that different radicals bonded to silicon via carbon atoms arise. The product of this reaction is then further randomly converted. In a third route, a silicic acid (hetero)polycondensate with identical radicals bonded to silicon via carbon atoms is used as the output material; however, the conversion to the product pursuant to the invention occurs in a non-random manner. The non-random reaction to the stage of the silane may occur with this route as well, whereas the product mix is subsequently subjected to hydrolytic condensation without being separated. A fourth route is based on two batches of a silane or silicic acid polycondensate that will be separately converted. In doing so, the first batch is converted with a different reagent (Y) than the second batch. The silanes derived in this manner are then co-condensed. Two, three or all four of these methods of the three specified routes may even be randomly combined with each other. We then achieve highly diversified mixed condensates.

One example for the fourth route is the use of cyclopentadiene as the first reagent (Y) and furan as the second reagent (Y).

For the non-random reactions, it is beneficial if the reagent (Y) or the reagent (Z) is used in a molar deficit based on the number of available groups B or B plus B' defined as 1−α mol of compound (Y) or (Z) in relation per mol of groups boron B plus B'. In this regard, α is preferably at least 0.05, preferably 0.10, in other cases at least 0.30, sometimes even at least 0.40, and in individual cases >0.50, whereas a can then even assume values of, e.g. 0.90.

This technical teaching is based on the fact that when using reagent (Y) or (Z) in a deficit, this compound is entirely consumed so that, potentially from a toxicological or allergenic perspective, problematic monomers are no longer present in the silicic acid (hetero)polycondensates pursuant to the invention or already in their preliminary stages (however, excess reagent (Y) can naturally also be removed potentially by simply applying negative pressure). And finally, a decisive benefit arises with production—the product of the reaction does not have to be cleaned or processed in any way and can therefore be immediately and easily used or subjected to a subsequent reaction.

The invention will be explained in more depth in the following based on examples of reactions.

As an output material, a silicic acid polycondensate is used in the first of these examples, which was produced through hydrolysis and condensation of a silane of general formula (B) (preferably in the "Sol-Gel" process):

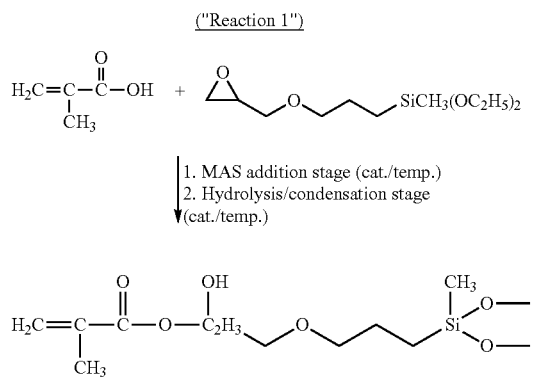

The resulting silicic acid polycondensate is depicted as "Base Resin I" in the following. It is then converted with a compound (Y) as described above, preferably with cyclopentadiene. This reaction is depicted as follows:

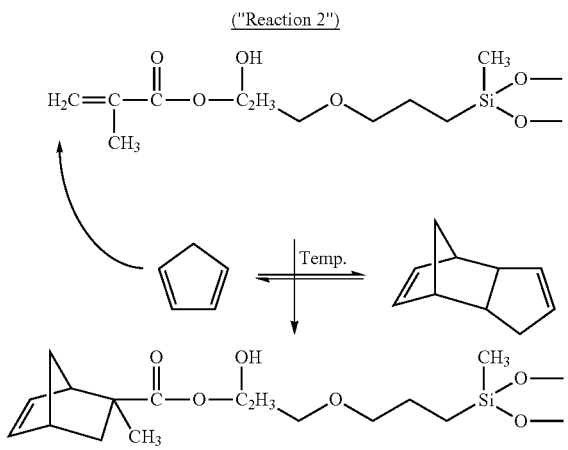

The product of this reaction—with a complete conversion—is a silicic acid (hetero)polycondensate, in which each Si atom has the same radical $R^3$. It contains a norbornenyl group as group $R^1$, which is bonded to radical $R^3$ via a C(O)O linkage group. In addition, it has a hydroxy group as radical $R^2$.

A condition for the complete conversion is an adequate amount of cyclopentadiene in the reaction mixture. If it is reduced, we will achieve a silicic acid polycondensate pursuant to the invention that contains two different radicals $R^3$:

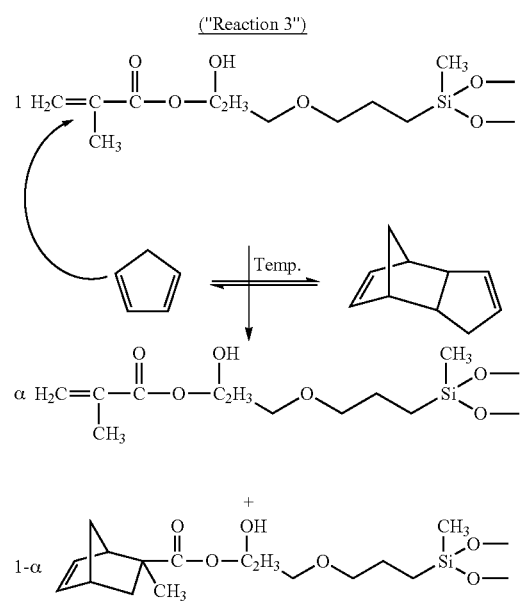

The first radical $R^3$ contains a methacrylate group as an organically polymerizable group, which is accessible to a thiol-ene polyaddition, though not to a ring-opening methathesis polymerization (ROMP). The second radical $R^3$ contains a norbornenyl group as an organically polymerizable group, which can additionally be subjected to a ROMP. Both radicals $R^3$ contain a hydroxy group as group $R^2$.

In this example, the generation of different radicals $R^3$ occurs in the last step. However, this is already possible in a previous step:

If the product of "Reaction 1" is connected with a reagent (Z), which converts the part or a part of hydroxy groups into organically polymerizable groups containing double bonds, in a sub-random manner prior to the reaction with reagent (Y) (in this case, cyclopentadiene), an additional fine gradation can be achieved. This is demonstrated in an example that is based on a silicic acid polycondensate, which was produced through hydrolytic condensation of a silane of a general formula (D). To achieve this, the condensate of general formula (B) is first modified through a reaction with methacrylic acid chloride as reagent (Z):

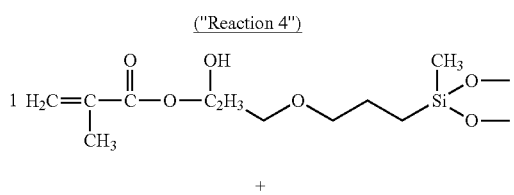

-continued

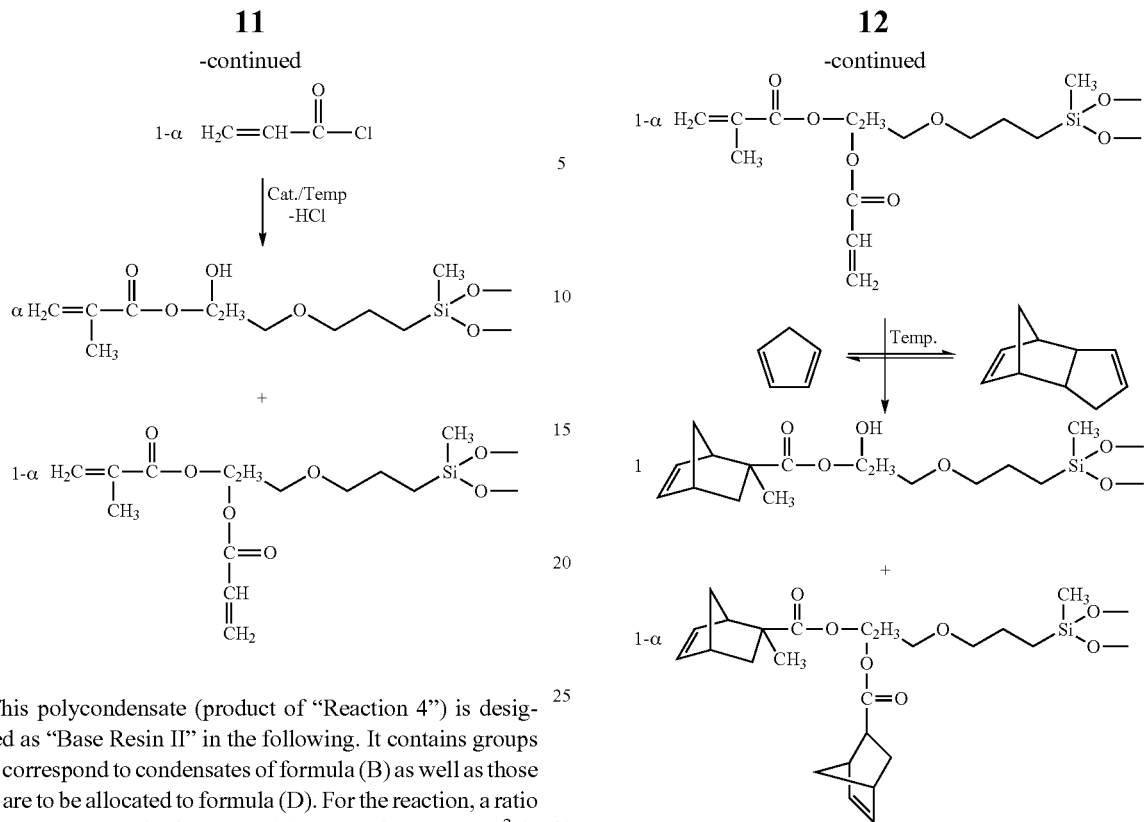

This polycondensate (product of "Reaction 4") is designated as "Base Resin II" in the following. It contains groups that correspond to condensates of formula (B) as well as those that are to be allocated to formula (D). For the reaction, a ratio of 0.6 to 0.95 mol of reagent (Z) converting group $R^2$ is preferably used, i.e. in this case, preferably 0.6 to 0.95 mol of an acrylic acid compound is used per mol of hydroxy group. Alternatively, the reaction with reagent (Z) converting group $R^2$ may occur in entirety, in which the acrylic acid compound is used to molar equivalence or, in some case, even beyond. However, the latter is frequently not beneficial with respect to the desire to avoid the presence of monomer radicals in resin. The formed silicic acid polycondensate then contains only radicals $R^3$ that have two organically polymerizable groups, which are not accessible to a ROMP. This variation is designated as "Reaction 5" in the following.

Both the product of "Reaction 4" as well as that of "Reaction 5" can therefore either be converted with an adequate amount of reagent (Y), such that all groups containing double bonds are converted into groups $R^1$ pursuant to the definition of the present invention. When using the product of "Reaction 4", we achieve a silicic acid polycondensate as a result, in which a part of the condensate has radicals $R^3$ with a (respectively identical) group $R^1$ (here a norbornenyl group), as well as has a hydroxy group as group $R^2$. An additional part of this condensate has other radicals $R^3$ bonded to silicon via a C-atom, which contain two norbornenyl groups (one non-substituted and one methyl-substituted):

("Reaction 6")

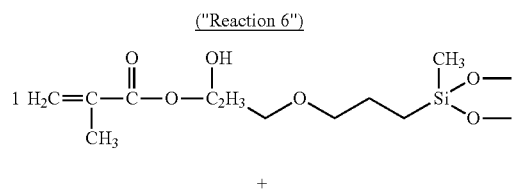

+

In contrast, with the product of "Reaction 5", we achieve a uniform condensate with this reaction, in which all radicals $R^3$ have two norbornenyl groups (n=0 and o=2 in formula (1) ("Reaction 7"). Alternatively, a deficit of reagent (Y) can be used, through which a further differentiation occurs when using the product of "Reaction 4"—the resulting silicic acid polycondensate contains five different radicals bonded to silicon via a carbon atom, namely those two that are shown as products in the previous reaction as well as the unconverted radicals and a radical $R^3$, which arose through a reaction of the radical containing a methacrylic group as well as an acrylate group having only one molar equivalent cyclopentadiene. Due to the fact that the acrylate group is significantly more reactive than the methacrylate group, a radical $R^3$ having a methacrylate group as group $R^2$ selectively arises in the process. This reaction is designated as "Reaction 8" in this case. If the production of "Reaction 5" is converted with a deficit of reagent (Y), we obtain, in contrast, two different radicals $R^3$. In the first radical $R^3$, only the acrylate group reacted with (Y); the radical contains one group $R^1$ and one group $R^2$. In the other radical $R^3$, both the methacrylate group as well as the acrylate group reacted with cyclopentadiene; the product contains two groups $R^1$ ("Reaction 9"). (The condition for this is that a molar share a of (Y), which is greater than the molar share of an acrylate group due to the fact that, as mentioned below, it abreacts first if insufficiently high temperatures are not selected).

In the case of the simultaneous present of acrylic and methacrylic radicals, the selectiveness of the reaction with reagent (Y) cannot simply be controlled by its amount, but rather by the temperature as well, at which the reaction occurs. Thus, primarily only the (reactive) acrylic groups of cyclopentadiene are connected at 50° C., although the (more inactive) methacrylic groups connect at 90° C.

The difference of reactivity between acrylic acid and methacrylic acid derivatives compared to reagent (A) can also be used in other random arrangements of the invention in order to selectively and specifically produce radicals $R^3$ with a group $R^1$ produced from the acrylic acid radical through a reaction with (Y) as well as a methacrylic radical as a group $R^2$.

Naturally, the previous reactions are only examples for potential principles pursuant to the invention; a number of variations are possible. Thus, instead of the silane of formula (B) for the production of the output material, one may be used, in which the methacrylate group is replaced by an acrylate group ("Base Resin III"). The product of this reaction ("Reaction 10") may be converted analogously to "Reaction 4" above with, e.g. an acrylic acid compound or even with a methacrylic acid compound. In the first case, a condensate emerges with radicals $R^3$ that have two identical organically polymerizable groups accessible to a thiol-ene reaction, which are not accessible to a ROMP; in the second case, there are two different such groups. They are in turn variably reactive. The first case is depicted below; it results in a product that is designated in the following as "Base Resin IV".

The base resin (III) is produced analogously to the above depiction of Reaction 1, thus it is not necessary to show it here in further detail. The reaction joins to that with the acrylic acid compound; the Base Resin IV emerges:

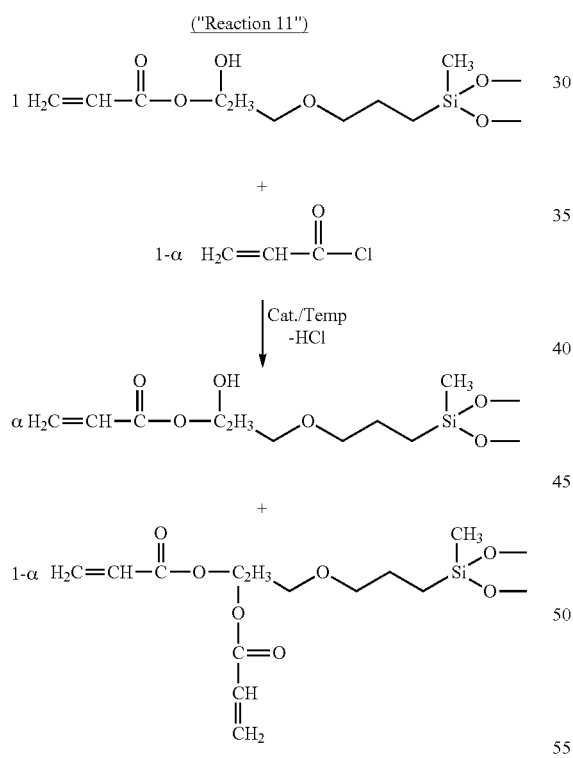

In this manner, a differentiated range of products can be created in turn because upon using cyclopentadiene in the deficit in addition to both unconverted radicals, which were described in connection with "Reaction 6", three radicals $R^3$ emerge that bear either two different groups $R^1$ (methyl-substituted and non-substituted norbornenyl) or two identical groups $R^1$ or one group $R^1$ in conjunction with one methacrylic group as group $R^1$, and two radicals emerge that respectively bear one other group $R^1$ (methyl-substituted and non-substituted norbornenyl) in conjunction with a hydroxy group as group $R^1$:

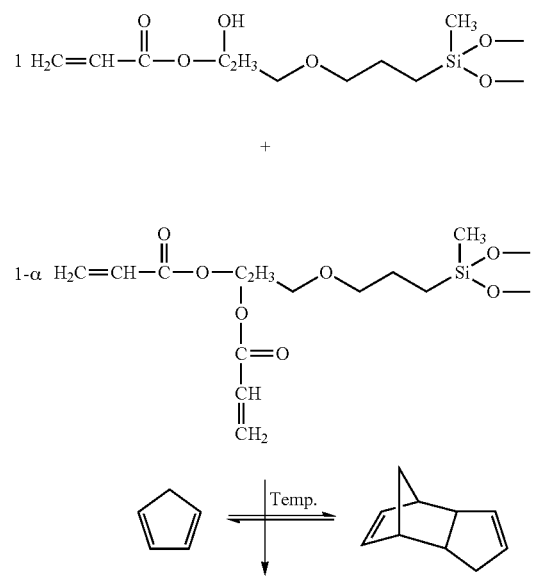

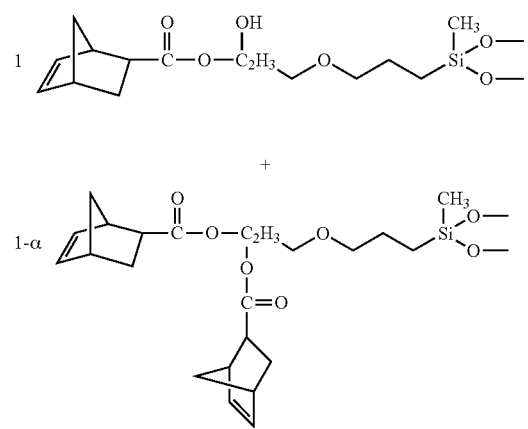

Of course, many other output materials are likewise suited for the invention. An additional example for the variation, in which a non-random preliminary reaction of four different radicals $R^3$ may occur, is the following reaction that is useful for the non-random reaction of a free hydroxy group:

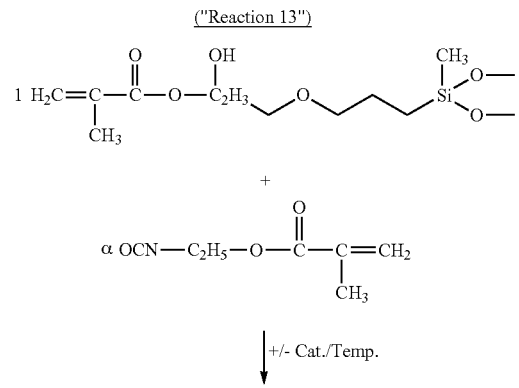

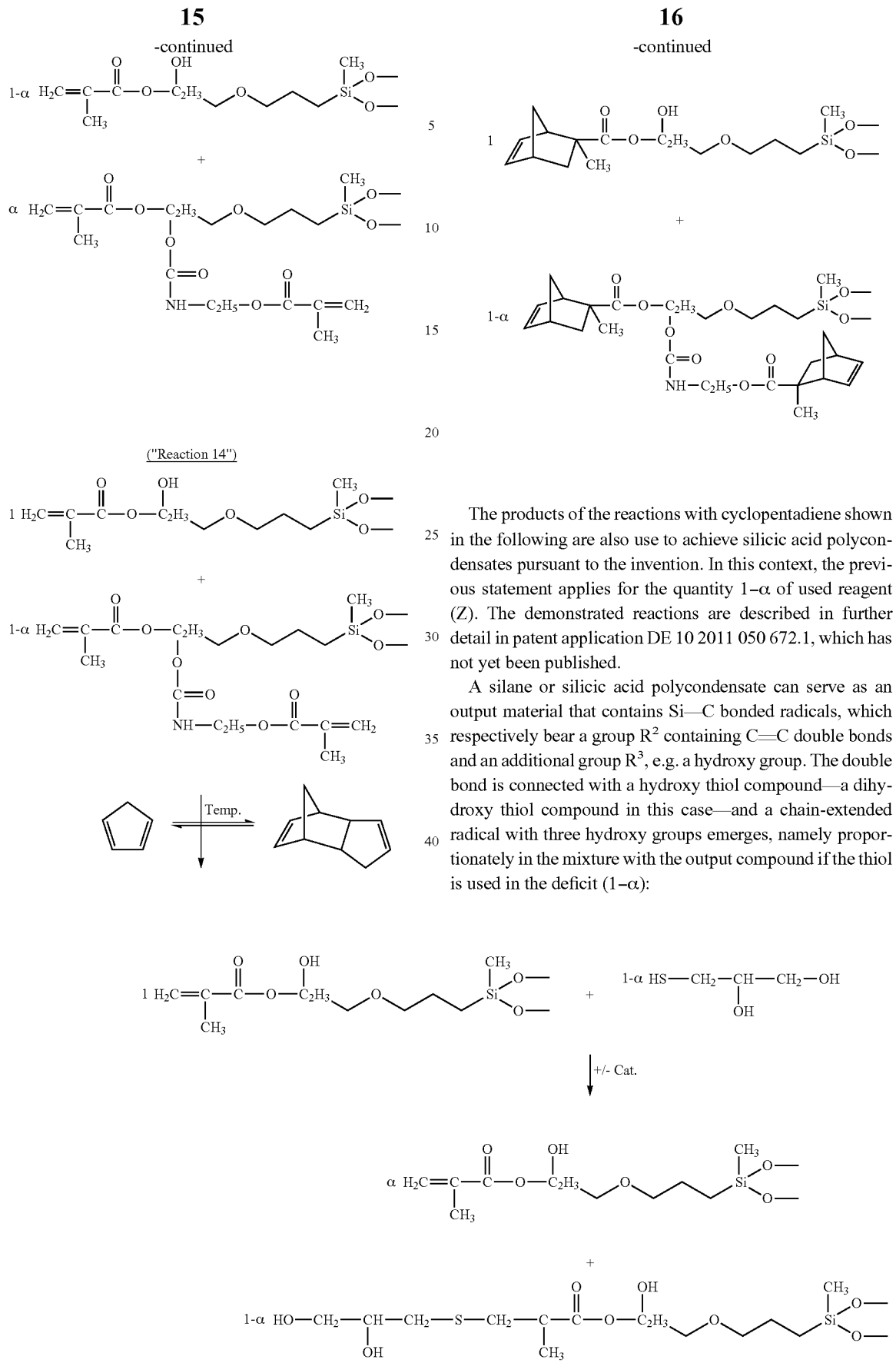

The products of the reactions with cyclopentadiene shown in the following are also use to achieve silicic acid polycondensates pursuant to the invention. In this context, the previous statement applies for the quantity $1-\alpha$ of used reagent (Z). The demonstrated reactions are described in further detail in patent application DE 10 2011 050 672.1, which has not yet been published.

A silane or silicic acid polycondensate can serve as an output material that contains Si—C bonded radicals, which respectively bear a group $R^2$ containing C=C double bonds and an additional group $R^3$, e.g. a hydroxy group. The double bond is connected with a hydroxy thiol compound—a dihydroxy thiol compound in this case—and a chain-extended radical with three hydroxy groups emerges, namely proportionately in the mixture with the output compound if the thiol is used in the deficit $(1-\alpha)$:

Through the reaction with an isocyanate containing C═C double bonds, the C═C double bond is reintroduced, though shifted largely relatively further outward, while the additional hydroxy group remains intact:
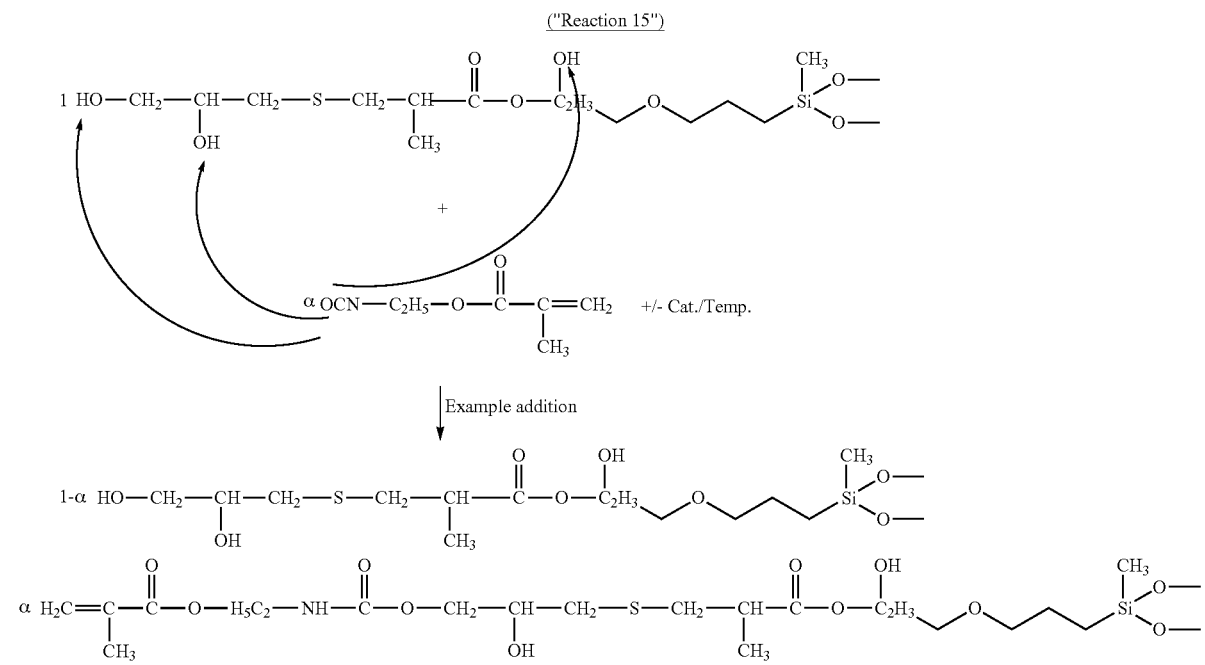
We obtain a similar product if the hydroxy group is converted with a reactant other than isocyanate, e.g. an anhydride:
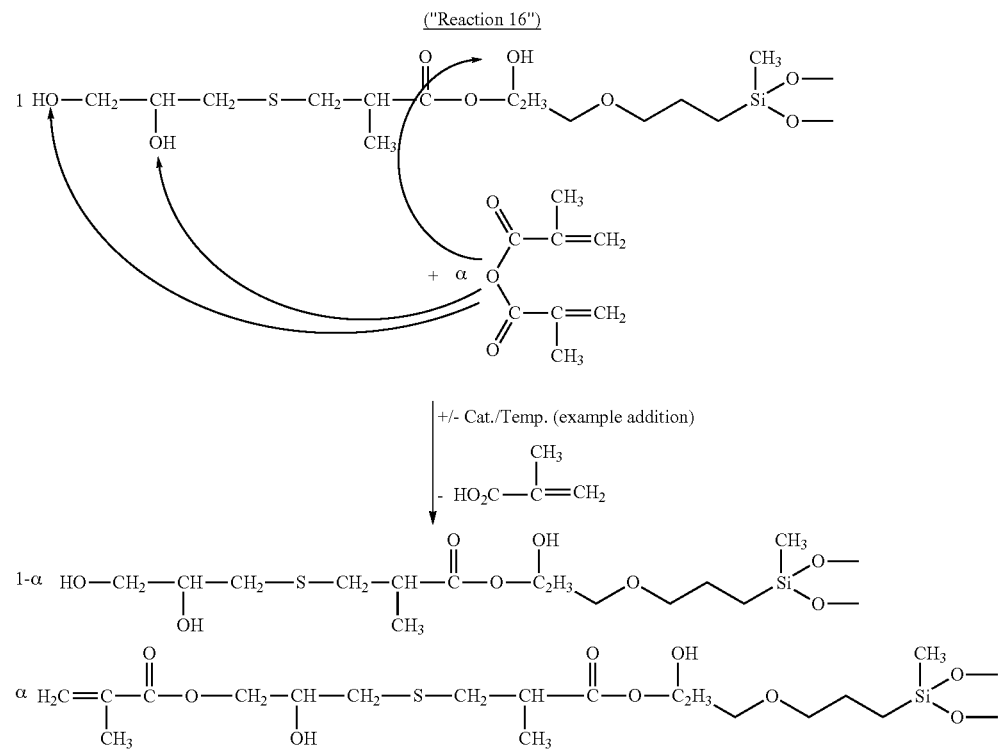

Of course, another reagent can be used for this reaction instead of a thiol, which can connect to C=C double bonds, for example an amine:

produced through a reaction of the reaction product of the following "Reaction 18" with the reagent (Y) (e.g. cyclopentadiene):

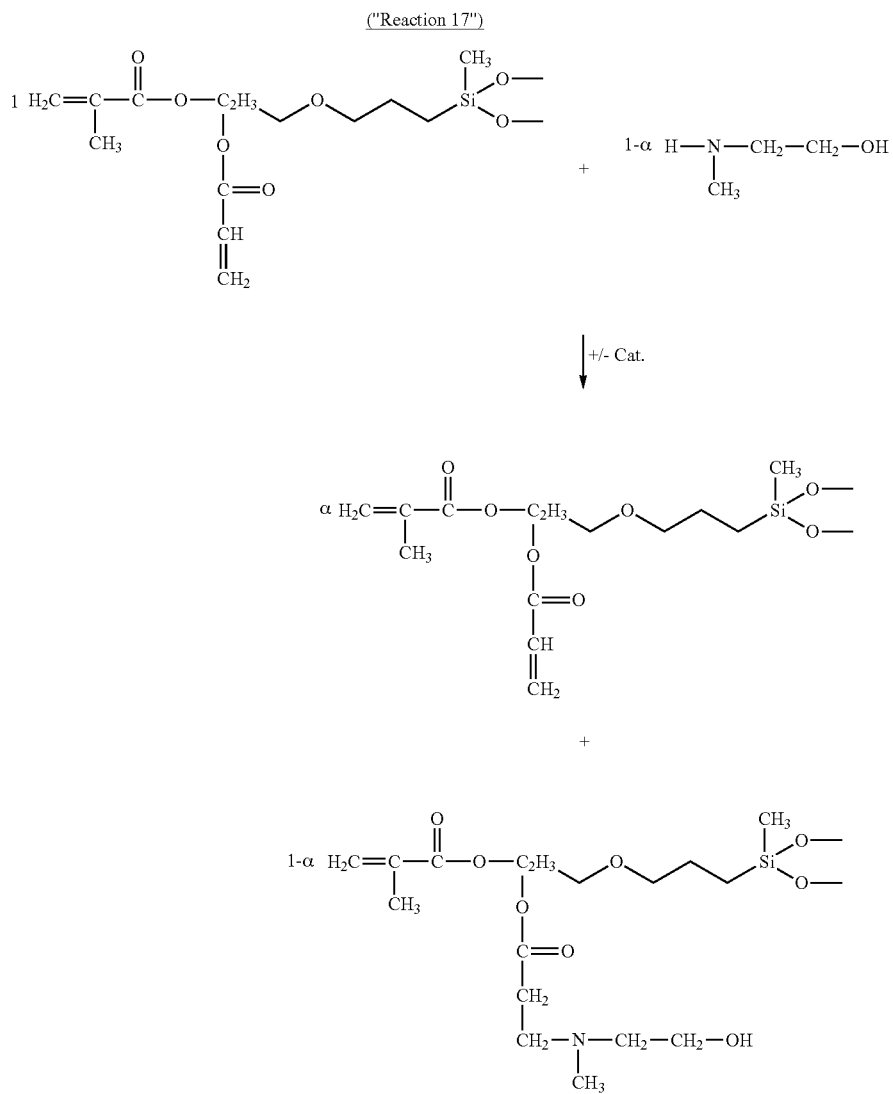

With all of these reactions, we can freely select the proportion between unconverted and converted radical $R^3$ by our choice of molar ratio of reagent (A). The same applies for the previous reaction with a reagent Z. As a result, we obtain a silicic acid polycondensate that has at least four different radicals $R^3$ bonded to silicon via a carbon atom. It becomes instantly apparent that, with this selection of the synthesis method, a variety of silicic acid polycondensates are available, which have different properties depending on the availability and share of different radicals $R^3$, although they were all achieved through a reaction with the same reagents.

Examples for silicic acid (hetero)polycondensates pursuant to the invention, in which $R^2$ represents a sulfonic acid group or a salt thereof, are for instance those that can be

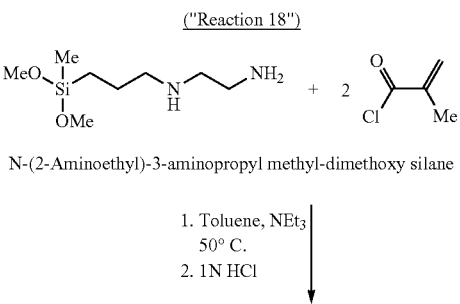

N-(2-Aminoethyl)-3-aminopropyl methyl-dimethoxy silane

1. Toluene, NEt$_3$
   50° C.
2. 1N HCl

-continued

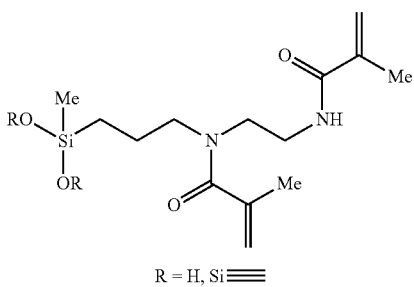

R = H, Si≡

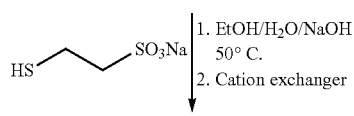

1. EtOH/H₂O/NaOH 50° C.
2. Cation exchanger

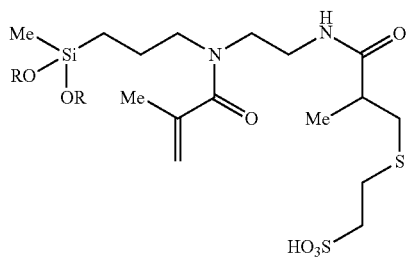

"Reaction 18" is described in patent application DE 10 2011 050 672.1, which has not yet been published. The substituents of silicon designated in the formula schema with Me and OR may be randomly selected as needed, i.e. a number of hydrolytically condensable radicals suitable for the desired silicic acid (hetero)polycondensate or radicals appearing as cross-link modifiers may be present. In specific embodiments, two hydrocarbon radicals bearing the reactive functions pursuant to the invention may be present; the sum of hydrolytically condensable radicals and radicals appearing as cross-link modifiers is then 2. The reaction with reagent (Y) leads to a product, in which the methacrylic acid amide group is converted into a group accessible to a ROMP (with the reaction with cyclopentadiene in a methyl norbornene group). The product falls under formula (1) with n equal to 1 and o equal to 1.

A silicic acid (hetero)polycondensate with n equal to 1 and o equal to 2, whereas both radicals R² are different and represent COOH and SO3H, can be produced with reagent (Y) through a reaction of the reaction product of "Reaction 19" shown in the following, as described below:

("Reaction 19")

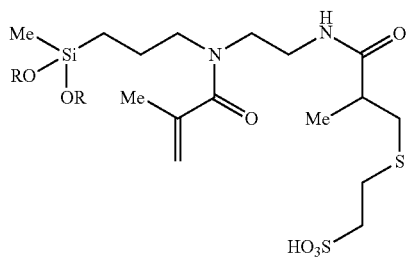

N-(2-Aminoethyl)-3-aminopropyl methyl-dimethoxy silane

EtAc
50° C.

-continued

R = H, Si≡

1. Na₂SO₃/H₂O
2. Cation exchanger

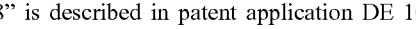

The reaction of the product of "Reaction 19" with reagent (Y) occurs as described for the previous reaction to the methacrylic amide group.

The silicic acid (hetero)polycondensates pursuant to the invention can be hardened through the reaction with di or polythiols within the scope of a thiol-ene reaction with groups containing double bonds. Furthermore, the double bonds in groups R² can, if present, be subjected to a carbon chain forming polymerization reaction (polyaddition; chain growth polyaddition), while groups R¹ can be subjected to a ROMP. Both of these reactions cause a hardening of the materials as well. And finally, the groups containing double bonds can be used to introduce additional reactive groups, such as OH groups, COOH groups or other acid functions, or even additional silyl groups into the condensate. The following, for instance, are suited for this: mercapto alcohols, mercapto thiols, mercapto boron acids, mercapto sulfonic acids or mercapto silanes (the last one for introducing additionally inorganically condensable groups). Examples for mercapto dioles are: 3-Mercapto propane-1,2-diol, 6-Mercapto-1-hexanol, 4-(Mercaptohexyloxy)-benzyl alcohol, 2- or 3- or 4-Mercapto phenol (solid), 11-Mercapto-1-undecanol, or 1-Mercaptoundec-11-yl)-tetraethylene glycol. Regardless of this, groups R² with the meaning OH or COOH in the polycondensate can be further converted, namely with an isocyanate or a compound containing epoxy groups or—only in the case of R² equal to OH—with an (activated) carboxylic acid.

Therefore, either further reactive groups can be added to the to the condensate as needed via linkage group B, which is an ester, ether, acid amide or urethane group depending on whether or not the compound connects to a hydroxy or a carboxyl group, for example, additional C=C double bonds, phosphorous groups like phosphoric acids/phosphorous acid ester, amino groups or sulfonic acid groups, which are added as substituents of isocyanate, the compound containing epoxy groups or the carboxylic acid, or eliminate previously present hydroxy or carboxylic acid groups, e.g. to decrease the hydrophily or reactivity of the condensate. If the reaction occurs in the deficit, additional fine gradations can be implemented.

The silicic acid (hetero)polycondensates or preliminary stages pursuant to the inventions can be mixed with any fillings (particles, fibers) prior to hardening, through which we achieve composites. Suitable fillings are those, e.g. which are described in DE 19643781, DE 19832965, DE 10018405, DE 10041038, DE 102005018351, and DE 102005061965. If necessary, very high filling contents can be achieved. The composites can normally be processed as plastics. In a hardened form, particularly with high filling contents, the composites demonstrates a high level of strength, very minimal shrinkage, excellent esthetics, as well as high biocompatibility. Their modulus of elasticity can be set to the desired values and they are free of monomers with the respective reaction control. In many areas, different properties can be finely adjusted and adapted to the respective requirements on all levels beginning with the silanes used as output materials and the unhardened, unfilled resins, the matrix systems to the filled systems (composites) in an unhardened and hardened form through the staged reactions, as the present invention demonstrates.

Thus use of materials pursuant to the invention extends to the use in the form of bulk materials, composites, cements, adhesives, grouting compounds, solvent-stabile, flexible sealants, coating materials, bonding agents, binding agents for ceramic particles (ceramic forming method), for the production or priming of fillings and fibers, as well as use in reaction extruders, etc.

The technical fields, in which the materials can be used, are not limited and extend, for example, from (micro) optics and (micro) electronics to medicine.

Use in the field of dentistry is particularly preferable, e.g. as a restoration or prophylaxis material, in prosthetics or as implant material: As such, the modulus of elasticity for different applications can be adjusted with a single basic material through minimal modifications of the substituents and/or the hardening reactions, as explained above, which can be particularly beneficial for applications in oral medicine (re-lining material, basic prosthetic material, artificial teeth, crowns/bridges, filling material, and the like). The materials can be advantageously used in medical industry as well, for example, as knee replacement material, bone cement, ear molds or other medical molded parts.

Due to the organically polymerizable groups, which are accessible to photopolymerization, the silicic acid (hetero) polycondensates can be subjected to multi-photon polymerization. With this technology, highly precise 2D or 3D molded parts can be produced form a bath material.

The invention is further explained on the basis of specific examples in the following:

EXAMPLE 1

Synthesis of Base Resin I ("Reaction 1"; Resin with Identical C—Si-Bonded Radicals with One Methacrylate and One Hydroxy Group)

For receiving 125.0 g (0.503 mol) of 3-Glycidyloxypropyltrimethoxysilane, 1.31 g (0.005 mol) of triphenylphosphine (as a cat.), 0.2% BHT by weight (as a stabilizer), and then 47.35 g (0.550 mol) of methacrylic acid are added drop-wise in a dry atmosphere and stirred at 80° C. (approx. 24 hrs.). The reaction can be followed by the decrease in the concentration of carboxylic acid via acid titration and the epoxy conversion can be followed via Raman spectroscopy/epoxy titration. The band of epoxy silane characteristic for the epoxy group appears in the Raman spectrum at 1256 cm$^{-1}$. The epoxy or carboxylic acid conversion is at ≥99% or ≥89% (→because 1:1.1 is a carboxylic acid surplus). After adding acetic ester (1000 ml/mol of silane) and $H_2O$ for hydrolysis with HCl (as a cat.), it is stirred at 30° C. The progress of the hydrolysis is respectively followed via water titration. Processing occurs approximately after multiple days of stirring through repeated extraction with aqueous NaOH and with water and filtration via hydrophobized filters. A rotary evaporator is used first and then an oil pump vacuum is used for suctioning. This resulted in a liquid resin without the use of reactive thinners (monomers) having a very low viscosity of approx. 3-6 Pa·s at 25° C. (heavily dependent upon exact hydrolysis and processing conditions) and 0.00 mmol of $CO_2H/g$ (no free carboxyl groups).

EXAMPLE 2

"Reaction 2" with a Molar Excess of (Y)=Cyclopentadiene ("CP") (Molar Ratio of Resin:CP=1:2; Production of a System with Uniform Radicals For receiving 80.0 g (0.30 mol) of Base Resin I, approx. 45.5 g (0.69 mol) of cyclopentadiene (CP) (freshly produced by separating dicyclopentadiene) are distilled while stirring at approx. 90° C. and then continually stirred for approx. 1-2 hours at 90° C. The reaction can be followed via NMR as well as via the decrease of the ν(C=C, methacrylic) bands (1639 cm$^{-1}$) and the formation and increase of the ν(C=C, norbornenyl) bands (1574 cm$^{-1}$) via Raman spectroscopy. The volatile components, such as unconverted cyclopentadiene, are extracted in an oil pump vacuum at temperatures up to 90° C. This resulted in a liquid resin having a viscosity of approx. 53-100 Pa·s at 25° C. (heavily dependent upon precise synthesis and processing conditions as well as the preliminary stages). Additional processing is normally not necessary.

EXAMPLE 3

"Reaction 3" with a Quantity of CP that is Insufficient for the Complete Reaction of the Double Bonds; Production of a Norbornene Methacrylic Mixed System For receiving 26.6 g (0.10 mol) of Base Resin I, approx. 9.94 g (0.15 mol) of cyclopentadiene (CP) (freshly produced by separating dicyclopentadiene) are distilled while stirring at approx. 90° C. and then continually stirred for approx. 1.25 hours at 90° C. The volatile components, such as unconverted cyclopentadiene, are removed in an oil pump vacuum at temperatures up to 90° C. This resulted in a liquid resin (X≈0.33) with a viscosity of approx. 29 Pa·s at 25° C. (heavily dependent upon precise synthesis and processing conditions as well as the preliminary stages). Additional processing is normally not necessary.

EXAMPLE 4

"Reaction 4"; Synthesis of Base Resin II while Using a Large Deficit of Acrylic Acid Chloride For receiving 120.1 g (0.45 mol) of Base Resin I and 35.1 g triethylamine (0.347 mol) in 450 ml THF as a solvent, 28.51 g (0.315 mol) of acrylic acid chloride are added drop-wise while stirring in a dry atmosphere and through cooling in an ice bath and continually stirred at room temperature. The reaction can be followed via NMR as well as via the decrease of acid chloride bands via IR spectrum. Following the usual processing for separating the amine hydrochloride arising upon being added and acidic byproducts as well as the extraction of the volatile components with the oil pump vacuum, a liquid resin emerges having a viscosity of approx. 1.5 Pa·s at 25° C. (heavily dependent upon precise synthesis and processing conditions, particularly the preliminary stages).

EXAMPLE 5

Synthesis of Base Resin II Through the Use of a Slight Deficit of Acrylic Acid Chloride For receiving 120.7 g (0.45 mol) of Base Resin I and 45.1 g of triethylamine (0.446 mol) in 450 ml of THF as a solvent, 36.66 g (0.405 mol) of acrylic acid chloride are added drop-wise while stirring in a dry atmosphere and through cooling in an ice bath and continually stirred at room temperature. Following the usual processing for separating the amine hydrochloride arising upon being added and acidic byproducts as well as the extraction of the volatile components with the oil pump vacuum, a liquid resin emerges having a viscosity of approx. 2.7 Pa·s at 25° C.

EXAMPLE 6

"Reaction 5"; Synthesis of Base Resin II Through the Use of a Minimal Excess of Acrylic Acid Chloride For receiving 133.3 g (0.50 mol) of Base Resin I and 63.8 g of triethylamine (0.63 mol) in 500 ml of THF as a solvent, 52.04 g (0.575 mol) of acrylic acid chloride are added drop-wise while stirring in a dry atmosphere and through cooling in an ice bath and continually stirred at room temperature. Following the usual processing for separating the amine hydrochloride arising upon being added and acidic byproducts as well as the extraction of the volatile components with the oil pump vacuum, a liquid resin emerges having a viscosity of approx. 3.3 Pa·s at 25° C.

EXAMPLE 7

"Reaction 6", Based on Base Resin II Pursuant to Example 4

For receiving 99.8 g (0.33 mol) of Base Resin II pursuant to Example 4, approx. 20.3 g (0.31 mol) of cyclopentadiene (CP) (previously freshly produced by separating dicyclopentadiene) are added drop-wise while stirring at approx. 50° C. After heating the reaction mixture to approx. 90° C., 43.0 g (0.65 mol) of CP (freshly produced by separating dicyclopentadiene) are distilled while stirring and then continually stirred for approx. 1.5 hours at 90° C. The reaction can be followed via NMR and via the decrease of the v(C=C, (meth) acrylic) bands (1639 cm$^{-1}$) as well as the formation and increase of the v(C=C, norbornenyl) bands (1577 cm$^{-1}$) via Raman spectroscopy. The volatile components, such as unconverted cyclopentadiene, are extracted in an oil pump vacuum at temperatures up to 90° C. This resulted in a liquid resin having a viscosity of approx. 185 Pa·s at 25° C. Additional processing is normally not necessary.

EXAMPLE 8

"Reaction 6", Based on Base Resin II Pursuant to Example 5

For receiving 92.4 g (0.03 mol) of Base Resin II, approx. 22.0 g (0.33 mol) of CP are added drop-wise while stirring at approx. 50° C. After heating the reaction mixture to approx. 90° C., 39.2 g (0.59 mol) of CP are distilled while stirring and then continually stirred for approx. 1.5 hours at 90° C. The volatile components, such as unconverted cyclopentadiene, are extracted in an oil pump vacuum at temperatures up to 90° C. This resulted in a liquid resin having a viscosity of approx. 380 Pa·s at 25° C. Additional processing is normally not necessary.

EXAMPLE 9

"Reaction 6", Based on Base Resin II Pursuant to Example 6

For receiving 111.5 g (0.35 mol) of Base Resin II, approx. 33.3 g (0.50 mol) of CP are added drop-wise while stirring at approx. 50° C. After heating the reaction mixture to approx. 90° C., 50.5 g (0.77 mol) of CP are distilled while stirring and then continually stirred for approx. 1 hour at 90° C. The volatile components, such as unconverted cyclopentadiene, are extracted in an oil pump vacuum at temperatures up to 90° C. This resulted in a liquid resin having a viscosity of approx. 1030 Pa·s at 25° C. Additional processing is normally not necessary.

EXAMPLE 10

Synthesis of Base Resin III

For receiving 203 g (0.816 mol) of 3-Glycidyloxypropyl-trimethoxysilane, 4.2 g (0.016 mol) of triphenylphosphine (as a cat.), 0.2% of BHT by weight (as a stabilizer), and then 74.9 g (1.04 mol) of acrylic acid are added drop-wise in a dry atmosphere and stirred at approx. 85° C. (approx. 24 h). The reaction can be followed by the decrease in the concentration of carboxylic acid via acid titration and the epoxy conversion can be followed via Raman spectroscopy/epoxy titration. The band of epoxy silane characteristic for the epoxy group appears in the Raman spectrum at 1256 cm$^{-1}$. After adding acetic ester (1000 ml/mol of silane) and H$_2$O for hydrolysis with HCl (as a cat.), it is stirred at 30° C. The progress of the hydrolysis is respectively followed via water titration. Processing occurs after multiple days of stirring through repeated extraction with aqueous NaOH and with water and filtration via hydrophobized filters. A rotary evaporator is used first and then an oil pump vacuum is used for suctioning. This resulted in a liquid resin without the use of reactive thinners (monomers) having a very low viscosity of approx. 4 Pa·s at 25° C.

EXAMPLE 11

"Reaction 11", Synthesis of Base Resin IV Through the Use of a Slight Deficit of Acrylic Acid Chloride For receiving 115.2 g (0.45 mol) of Base Resin III and 45.1 g of triethylamine (0.345 mol) in 450 ml of THF as a solvent, 36.7 g (0.405 mol) of acrylic acid chloride are added drop-wise while stirring in a dry atmosphere and through cooling in an ice bath and continually stirred at room temperature. The reaction can be followed via NMR as well as via the decrease of acid chloride bands via IR spectrum. Following the usual processing for separating the amine hydrochloride arising upon being added and acidic byproducts as well as the extraction of the volatile components with the oil pump vacuum, a liquid resin emerges having a viscosity of approx. 2.4 Pa·s at 25° C.

EXAMPLE 12

"Reaction 12"; Reaction of Base Resin IV with Cyclopentadiene

For receiving 94.4 g (0.323 mol) of Base Resin IV, approx. 20.3 g (0.31 mol) of cyclopentadiene (CP) (freshly produced by separating dicyclopentadiene) are distilled while stirring at approx. 50° C. and then continually stirred for approx. 1 hour at 50° C. The reaction can be followed via NMR and via the decrease of the ν(C=C, (acrylic) bands (1638 cm$^{-1}$) and the formation and increase of the ν(C=C, norbornenyl) bands (1576 cm$^{-1}$) via Raman spectroscopy. The volatile components, such as unconverted cyclopentadiene, are extracted in an oil pump vacuum at temperatures up to 50° C. This resulted in a liquid resin having a viscosity of approx. 131 Pa·s at 25° C. (heavily dependent upon precise synthesis and processing conditions as well as the preliminary stages). Additional processing is normally not necessary.

The invention claimed is:
1. Silicic acid (hetero)polycondensate comprising structural units of a following formula (1)

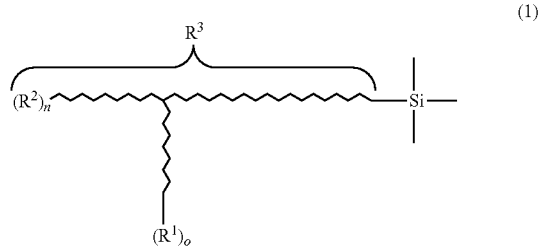

(1)

in which radicals, indices, and bonding symbols have the following meaning:
$R^1$ refers to a group that is available to a thiol-ene polyaddition when a thiol is added and can also be polymerized by a ROMP (ring opening metathesis polymerization),
$R^2$ is selected from
(a) organically polymerizable groups which are available to a thiol-ene polyaddition when a thiol is added, but not to a ROMP,
(b) —COOR$^8$ with R$^8$ equal to R$^4$ or $M_{1/x}^{x+}$,
(c) —OH or COOH, and
(d) —(O)$_b$P(O)(R$^5$)$_2$, in which b is equal to 0 or 1, —SO$_3$M$_{1/x}^{x+}$, NR$^7_2$ or NR$^7_3{}^+$,
wherein
$M^{x+}$ is an x-fold positively charged metal cation,
$R^4$ is a non-substituted or substituted hydrocarbon radical,
Radicals $R^5$ independently from each other represent a non-substituted or substituted hydrocarbon radical or OR$^6$, and
$R^6$ is hydrogen or a non-substituted or substituted hydrocarbon radical,
$R^7$ has either the same meaning as $R^4$, or two radicals $R^7$ together represent a divalent, substituted or non-substituted, saturated or unsaturated hydrocarbon group, $R^3$ represents a radical bonded to a silicon atom of said formula (1) by a carbon atom, to which said radical R$^1$ is bonded o-fold and said radical R$^2$ is bonded n-fold and which is equivalent or has different meanings in the same condensate,
each of the indices n and o represents 0, 1, 2 or greater than 2 with the stipulation that n+o represents at least 2,
at least one of the three bonds of the Si atom not further identified represents an oxygen bridge to an additional silicon atom or optionally to another metal atom, while the other two bonds either have the same meaning or instead represent an OH group, a hydrolysable group, or a radical bonded the said silicon atom via carbon,
wherein
each radical R$^3$ of said structure (1) must have at least one group R$^1$ or one group R$^2$ having the meaning specified in (a), wherein,
if said radicals R$^3$ are equal,
(x) each radical has at least one group R$^1$ and either one group R$^2$ with the meaning specified in (a) or a second group R$_1$, whereas in both cases, n must be at least 1 or
(xx) if, in addition, n is equal to 0, at least two groups R$^1$ have a different meaning, and
if said radicals R$^3$ are different, a first part of the radicals has at least one group R$^1$ and one of the following two conditions must be complied with:
(x) an additional part of the radicals has at least one group R$^2$ with the meaning specified in (a) or (d), and
(xx) two different radicals R$^3$ each have at least one group R$^1$.
2. Silicic acid (hetero)polycondensate according to claim 1, in which each radical R$^3$ has at least two different reactive organically polymerizable groups, from which at least one such group is accessible to a ROMP.
3. Silicic acid (hetero)polycondensate according to claim 1, in which different radicals R$^3$ are present, which have at least one group R$^1$ as well as at least one group R$^2$, whereas at least said groups R$^2$ differ from each other in different radicals R$^3$.
4. Silicic acid (hetero)polycondensate according to claim 1, in which each radical R$^3$ has at least two groups R$^1$ and one group R$^2$, which may be different in different radicals R$^3$.
5. Silicic acid (hetero)polycondensate according to claim 1 with different radicals R$^3$, in which n is greater than or equal to 1 and o is greater than or equal to 1 in a first part of said radicals R$^3$ and n is greater than or equal to 2 and o is equal to 0 in a second part of said radicals R$^3$.
6. Silicic acid (hetero)polycondensate according to claim 1, in which R$^1$ is selected from groups

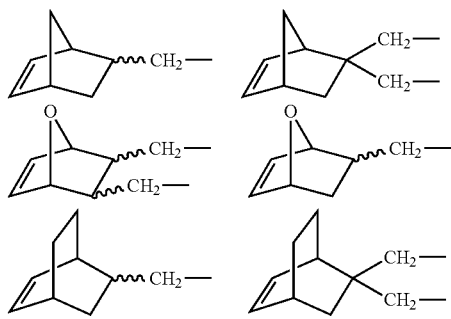

and/or $R^2$ is selected from groups containing C=C double bonds accessible to a thiol-ene addition.

7. Silicic acid (hetero)polycondensate according to claim 1 containing at least two different groups $R^2$, from which one is selected from said groups specified in (a) and a second one is selected from the members of the groups specified in (b) to (d).

8. Silicic acid (hetero)polycondensate according to claim 7 containing at least one group $R^2$ with the meaning of OH.

9. Process for the production of a silicic acid (hetero) polycondensate containing structural units of said following formula (1):

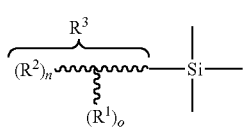 (1)

in which the radicals, indices, and bonding symbols have the following meaning:
$R^1$ refers to a group that is available to a thiol-ene polyaddition when a thiol is added and can also be polymerized by a ROMP (ring opening metathesis polymerization),
$R^2$ is selected from
(a) organically polymerizable groups which are available to a thiol-ene polyaddition when a thiol is added, but not to a ROMP,
(b) —$COOR^8$ with R equal to $R^4$ or $M_{1/x}^{x+}$,
(c) —COOH or —OH, and
(d) —$(O)_b P(O)(R^5)_2$, in which b is equal to 0 or 1, —$SO_3 M_{1/x}^{x+}$, $NR^7_2$ or $NR^7_3{}^+$,
whereas
$M^{x+}$ is an x-fold positively charged metal cation,
$R^4$ is a non-substituted or substituted hydrocarbon radical,
Radicals $R^5$ independently from each other represent a non-substituted or substituted hydrocarbon radical or $OR^6$ and
$R^6$ is hydrogen or a non-substituted or substituted hydrocarbon radical,
$R^7$ has either the same meaning as $R^4$ or two radicals $R^7$ together represent a divalent, substituted or non-substituted, saturated or unsaturated hydrocarbon group,
$R^3$ represents a radical bonded to the silicon atom of said formula (1) by a carbon atom, to which the radical $R^1$ is bonded o-fold and the radical $R^2$ is bonded n-fold and which is equivalent or has different meanings in the same condensate,
each of the indices n and o represents 0, 1, 2 or greater than 2 with the stipulation that n+o represents at least 2,
at least one of the three bonds of the Si atom not further identified represents an oxygen bridge to an additional silicon atom or optionally to another metal atom, while the other two bonds either have the same meaning or instead represent an OH group, a hydrolysable group, or a radical bonded the said silicon atom via carbon,
whereas
each radical $R^3$ of said structure (1) must have at least one group $R^1$ or one group $R^2$ having the meaning specified in (a), wherein,
if said radicals $R^3$ are equal, each radical $R^3$ has at least one group $R^1$
and if said radicals $R^3$ are different, a first part of said radicals $R^3$ has at least one group $R_1$, wherein a silicic acid (hetero)polycondensate having structural units (2),

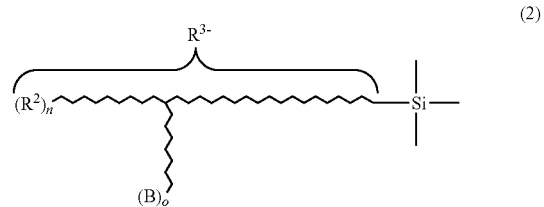 (2)

in which said groups $R^2$ and said indices n and o as well as said bonds of said silicon atom are defined as for the structural unit (1), and $R^{3'}$ designates a radical bonded to said silicon atom of said formula (1) via a carbon atom, to which the radical B is bonded o-fold and the radical $R^2$ is bonded n-fold and which is identical or has different meanings in the same condensate, or wherein said silane with said formula (2), in which the group $R^2$ and the indices n and o are defined for the structural unit (1) and the three bonds of said silicon atom represent an OH group, a hydrolysable group or a radical bonded to said silicon atom via a carbon atom and $R^{3'}$ designates a radical that is bonded to said silicon atom of said formula (1) via a carbon atom, to which said radical $R^1$ is bonded o-fold and the radical $R^2$ is bonded n-fold, whereas, in all cases, B is a straight-chain or branched organic group having at least one C=C double bond, is converted with a reagent (Y), which is selected from cyclopentadiene, furan, cyclohexadiene and materials, from which one of these three compounds may be formed in situ.

10. Process according to claim 9 for the production of a silicic acid (hetero)polycondensate comprising structural units of said formula (1) as defined in one of the claims 1 to 8.

11. Process according to claim 9, wherein a silicic acid (hetero)polycondensate of said structure (2) is used as a starting material in which different radicals $R^{3'}$ are present, wherein a first part of said radicals has at least one group B and one of the two following conditions must be complied with:
(x) an additional part of said radicals has at least one group $R^2$ with the meaning specified in (a) or (d),
(xx) two different radicals $R^3$ each have at least one group B, which vary preferably at the different radicals $R^{3'}$.

12. Process according to claim 9, wherein a silane or different silanes of said structure (2) is/are used as a starting material, and said silane or silanes is/are subjected to a hydrolytic co-condensation following the reaction with the reagent (Y), whereas one of the following conditions must be complied with:
(x) said different silanes are converted with said same reagent (Y), whereas the co-condensation is performed prior to, during or after the reaction with (Y), or
(xx) said silane is divided into two or more batches and each of these batches is separately converted with a different reagent (Y), upon which said achieved silanes are co-condensed.

13. Process according to claim 9, wherein said reagent (Y) is used in relation to said existing groups B in the deficit.

14. Process for the organic polymerization of a silicic acid (hetero)polycondensate according to claim 1, wherein said groups $R^1$ are subjected to a ROMP.

15. Process for the organic polymerization of a silicic acid (hetero)polycondensate according to claim 1 containing groups $R^2$ having the meaning specified in (a), wherein said condensate is converted with a di- or a polythiol.

16. Process for the organic polymerization of a silicic acid (hetero)polycondensate according to claim 1 containing groups $R^2$ having the meaning specified in (a), wherein said C=C double bonds contained in said groups $R^2$ are polymerized by a polyaddition.

17. Process for the modification of a silicic acid (hetero)polycondensate according to claim 1 containing groups $R^2$ having the meaning specified in (c), wherein it is converted with an isocyanate or a compound containing epoxy groups or, exclusively in the case of $R^2$ equal to OH, is converted with an (activated) carboxylic acid.

18. Process according to claim 17, wherein said isocyanate, said compound containing epoxy groups or said (activated) carboxylic acid is used in the deficit relative to the quantity of said present groups R.

19. Silicic acid (hetero)polycondensate according to claim 2 with different radicals $R^3$, in which n is greater than or equal to 1 and o is greater than or equal to 1 in a first part of said radicals $R^3$ and n is greater than or equal to 2 and o is equal to 0 in a second part of said radicals $R^3$.

20. Silicic acid (hetero)polycondensate according to claim 3 with different radicals $R^3$, in which n is greater than or equal to 1 and o is greater than or equal to 1 in a first part of said radicals $R^3$ and n is greater than or equal to 2 and o is equal to 0 in a second part of said radicals $R^3$.

21. Silicic acid (hetero)polycondensate according to claim 4 with different radicals $R^3$, in which n is greater than or equal to 1 and o is greater than or equal to 1 in a first part of said radicals $R^3$ and n is greater than or equal to 2 and o is equal to 0 in a second part of said radicals $R^3$.

\* \* \* \* \*